United States Patent [19]

Tyagi

[11] Patent Number: 5,755,660
[45] Date of Patent: May 26, 1998

[54] COMBINATION SURGICAL RETRACTOR, LIGHT SOURCE, SPREADER, AND SUCTION APPARATUS

[76] Inventor: Narendra S. Tyagi, 4209 Margate, Bloomfield Hills, Mich. 48302

[21] Appl. No.: 551,203

[22] Filed: Oct. 31, 1995

[51] Int. Cl.⁶ .................................................. A61B 11/02
[52] U.S. Cl. ........................... 600/205; 600/232; 600/245
[58] Field of Search .................................. 600/232, 231, 600/233, 227, 201, 205, 245

[56] References Cited

U.S. PATENT DOCUMENTS

| | | | |
|---|---|---|---|
| 1,706,500 | 3/1929 | Smith | 600/245 X |
| 3,227,156 | 1/1966 | Gauthier | 600/232 X |
| 3,384,078 | 5/1968 | Gauthier | |
| 3,522,799 | 8/1970 | Gauthier | |
| 3,626,471 | 12/1971 | Florin | 600/205 |
| 3,680,546 | 8/1972 | Asrican | 600/245 X |
| 4,185,634 | 1/1980 | Freedman | |
| 4,421,107 | 12/1983 | Estes | |
| 4,562,832 | 1/1986 | Wilder et al. | 600/205 X |
| 5,147,371 | 9/1992 | Washington | |
| 5,159,921 | 11/1992 | Hoover | |
| 5,167,223 | 12/1992 | Koros | |
| 5,224,931 | 7/1993 | Kumar | |
| 5,299,563 | 4/1994 | Seton | |
| 5,320,627 | 6/1994 | Sorensen | |
| 5,321,416 | 6/1994 | Spaeth | |
| 5,329,943 | 7/1994 | Johnson | |
| 5,375,481 | 12/1994 | Cabrera et al. | 600/233 X |
| 5,383,886 | 1/1995 | Kensey | |
| 5,392,787 | 2/1995 | Yoon | |
| 5,400,774 | 3/1995 | Villalta et al. | 600/232 X |

FOREIGN PATENT DOCUMENTS

| | | |
|---|---|---|
| 0552980 | 7/1993 | European Pat. Off. |
| 1222251 | 4/1986 | U.S.S.R. |
| 1697795 | 12/1991 | U.S.S.R. |
| WO9203099 | 3/1992 | WIPO |

OTHER PUBLICATIONS

Tyagi et al., "A New Minimally Invasive Technique For Cholecystectomy", Annals of Surgery, vol. 220, No. 5, Nov. 1994, pp. 617–625.

*Primary Examiner*—Jeffrey A. Smith
*Attorney, Agent, or Firm*—Weiner, Carrier, Burt & Esser, P.C.; Pamela S. Burt; Irving M. Weiner

[57] ABSTRACT

An apparatus and method of performing a cholecystectomy procedure through a 3-centimeter incision in the minimum stress triangle through the falciform ligament which provides for direct vertical view of the biliary ducts during dissection. Special tools are provided for this type and other types of surgical operations including obtuse-angled retractors having optionally fixed thereto lighting devices and/or suction devices.

18 Claims, 3 Drawing Sheets

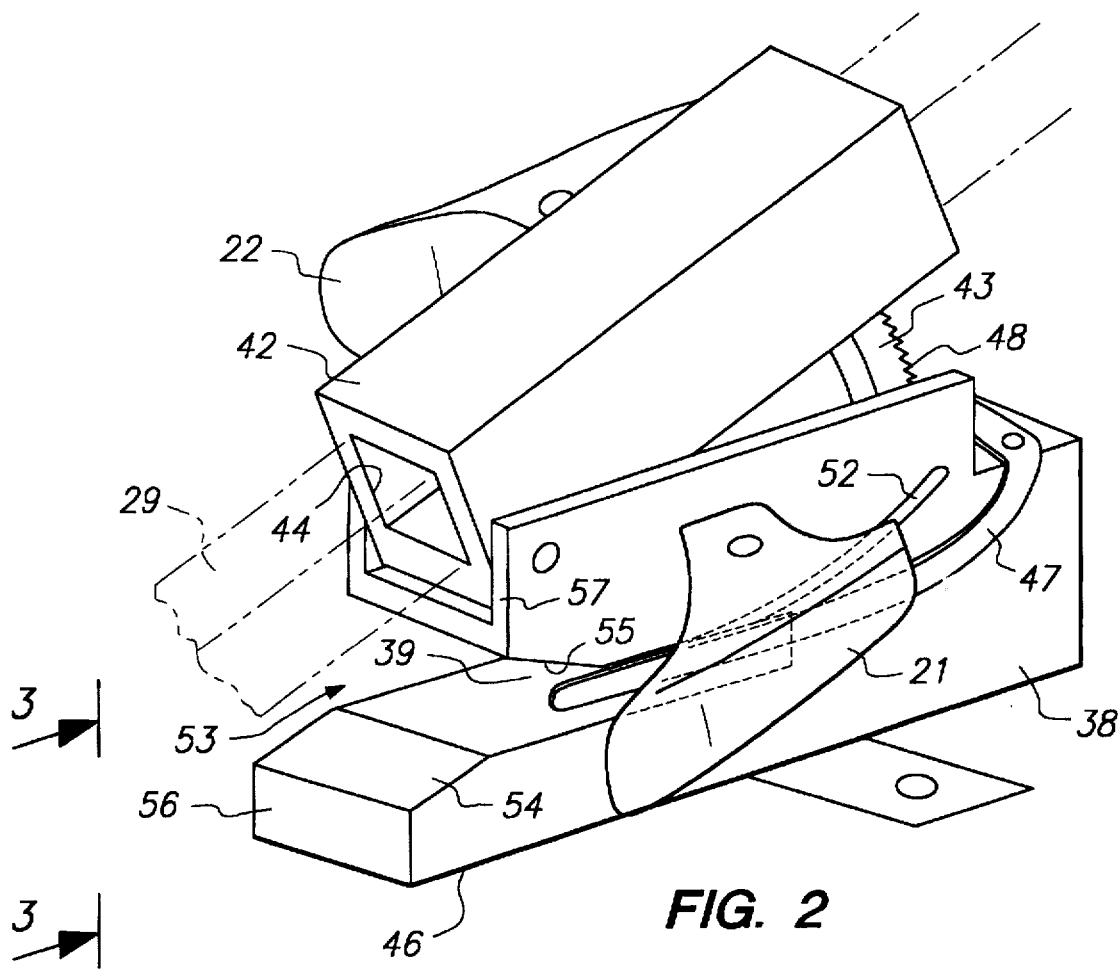
FIG. 2
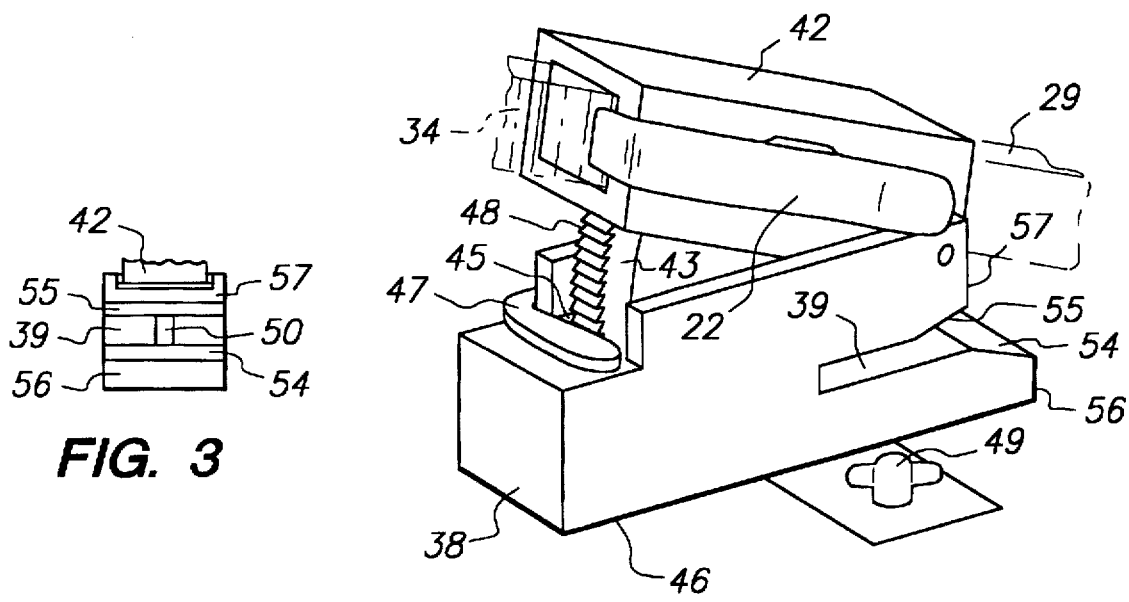
FIG. 3
FIG. 4

COMBINATION SURGICAL RETRACTOR, LIGHT SOURCE, SPREADER, AND SUCTION APPARATUS

FIELD OF THE INVENTION

This invention relates to a combination surgical retractor, light source, spreader, and suction apparatus; a finger-controllable securement apparatus; and a minimally invasive cholecystectomy surgical procedure.

BRIEF DESCRIPTION OF RELEVANT ART

With the introduction of laparoscopic cholecystectomy, a minimally invasive procedure, cholecystectomy has evolved to an outpatient procedure. Patients are able to return to preoperative functional status rapidly with minimal postoperative morbidity and pain. The laparoscopic procedure has gained acceptance because of the cosmetic desirability of the small size of the scar. However, there have been reports of various complications, including damage to the abdominal blood vessels, bowel laceration, and common bile duct injuries, associated with this technique. Biliary leakage and complications, including thermal injury to the common bile duct and the porta hepatis and ductal injury caused by blunt and sharp dissection near the cystohepatic angle, are associated with laparoscopic cholecystectomy. Conversion to open conventional cholecystectomy is required for patients who are undergoing laparoscopic procedures who have acute cholecystitis, densely adherent gallbladders, and large stones that require added manipulations. Patients with severe chronic obstructive pulmonary disease and aneurysms of the abdominal aorta are not candidates for laparoscopic cholecystectomies.

It is a desideratum of the present invention to avoid the animadversions of prior equipment and techniques. The microceliotomy approach for cholecystectomy of the present invention was designed to provide the advantages of a minimally invasive procedure, while requiring the minimum of persons to assist the surgeon and offering the potential for minimizing complications associated with laparoscopic cholecystectomy.

SUMMARY OF THE INVENTION

The invention provides a combination self-retaining surgical retractor, lighting device, and suction means apparatus, comprising: a substantially stationary toothed arm having a first end and a second end; a toothed cross bar also having a first end and a second end; said toothed cross bar first end being secured to said first end of said substantially stationary toothed arm in a generally perpendicular relation and forming a generally L-shaped section; a moveable toothed arm having a first end and a second end; said first end of said moveable toothed arm having a housing with a slotted opening which is attachable to said toothed cross bar and is laterally moveable along the length of said cross bar; a plurality of self-retaining surgical retractors; a lighting device which is unitary with at least one of said self-retaining surgical retractors; suction means which is unitary with at least one of said self-retaining surgical retractors; each of said self-retaining surgical retractors being releasably securable to said substantially stationary toothed arm, said toothed cross bar, or said moveable toothed arm.

The invention also provides securement apparatus for selectively securing two external members relative to each other, comprising: a first housing having a first channel therein for securement to a first external member having teeth disposed along at least one edge thereof; a second housing pivotally secured to said first housing; said second housing having a toothed sector depending therefrom and being provided with a channel through which a second external member having sawtooth teeth disposed along one side thereof may be disposed; said second housing being provided with a first finger-activatable control mechanism which permits releasably locking and unlocking of said second external member in a desired position relative to said second housing; said first finger-activatable control mechanism being disposed on a first side of said second housing; a second finger-activatable control mechanism being disposed on a second side of said second housing which is opposite to said first side thereof; said first housing having a second channel therein for accommodating said toothed sector and being dimensional so that no portion of said toothed sector will protrude through a surface of said first housing which is remote from said second housing; said first housing being provided with a spring-biased latching member which is adapted to releasably latch with the teeth of said toothed sector; and said second finger-activatable control mechanism being operable to move said spring-biased latching member.

The invention also provides a minimally invasive cholecystectomy surgical procedure eschewing the use of large incisions, comprising the steps of: making a small transverse high subxiphoid incision in the minimal stress triangle anterior to Calot's triangle to provide a direct vertical view of the biliary ducts during dissection; said small incision being less than approximately six centimeters; entering through said incision and through the falciform ligament into the peritoneal cavity; transacting the cystic duct and the cystic artery; isolating structures in the porta-hepatis; inserting through said incision self-retaining microceliotomy retractors with attached light and suction carriers to optimize the level of lighting in the operative field for safe dissection; and dissecting the gall bladder from the liver bed.

BRIEF DESCRIPTION OF THE DRAWINGS

FIG. 2 is an exploded perspective view of a finger-operated securement apparatus according to the invention.

FIG. 3 is a partial fragmentary view taken along the line 3—3 shown in FIG. 2 to show the unitary pin which mates with the concavities between the teeth in the stationary arm, the tooth cross bar, and the moveable tooth arm.

FIG. 4 is an exploded perspective view of the FIG. 2 device taken from another angle.

DETAILED DESCRIPTION

In accordance with a preferred embodiment of the invention, cholecystectomy may be performed preferably, but not necessarily, from the left side of the table through a 3-centimeter transverse skin incision located on the right side of the midline at the level of the base line of the minimal stress triangle (MST). Alternatively, a right subcostal incision may be used. Patients weighing more than 250 pounds may require a larger 4 to 5-centimeter incision to avoid problems with depth perception caused by "tunnel effect" encountered in obese patients.

Figure 1:
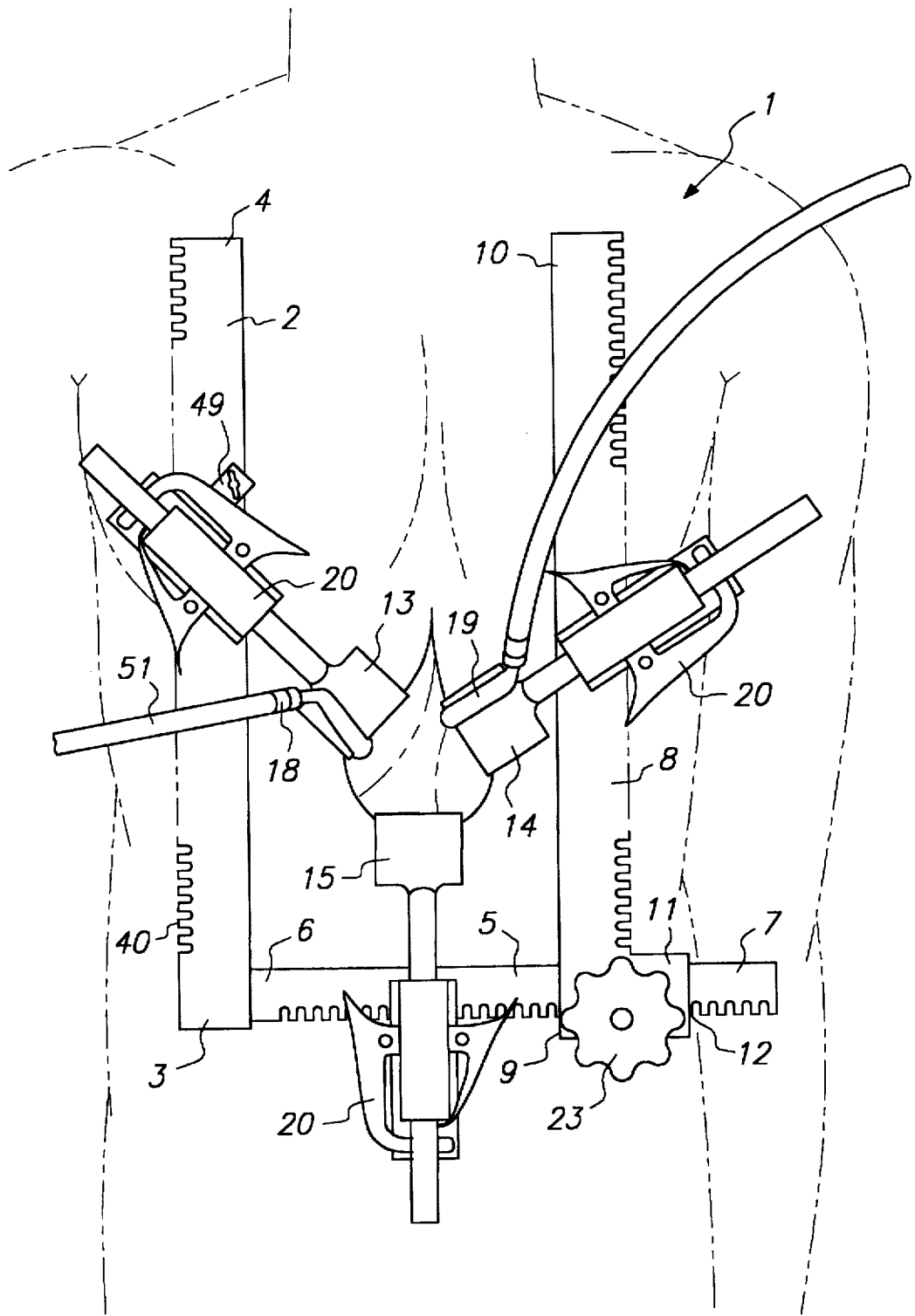
FIG. 1 is a top plan view of a patient undergoing surgery using the combination apparatus according to the invention.

FIG. 1 shows a preferred embodiment of a combination self-retaining surgical retractor, lighting device, and suction means apparatus 1 according to the present invention. The apparatus 1 includes a substantially stationary toothed rack or arm 2 having a first end 3 and a second end 4. There is provided a toothed cross bar 5 also having a first end 6 and a second end 7. The first end 6 of the toothed cross rack or bar 5 is secured to the first end 3 of the stationary toothed arm 2 in a generally perpendicular relation and forming a general L-shaped section.

The apparatus 1 also includes a moveable toothed rack or arm 8 having a first end 9 and a second end 10. The first end 9 of the moveable toothed arm 8 has a housing 11 with a slotted opening 12 which is attachable to the toothed cross bar 5 and is laterally moveable along the length of the cross bar 5.

The apparatus 1 also includes a plurality of self-retaining surgical retractors 13–17. A lighting device 18 is provided unitary with at least one of the retractors 13. Suction means 19 are also provided unitary with at least one of the retractors 14. Each of the retractors 13–17 is releasably securable to the stationary toothed arm 2, the toothed cross bar 5, or the moveable toothed arm 8.

The apparatus 1 also includes securement means 20 for releasably and moveably securing an associated retractor 13, 14, 15, 16 or 17 to the stationary toothed arm 2, the cross bar 5, or the moveable toothed arm 8. The securement means 20 permits moveable positioning of the associated retractor including pivotal motion of the associated retractor with respect to a plane containing the stationary toothed arm 2, the toothed cross bar 5, and the moveable toothed arm 8.

The apparatus 1 also includes first finger-activatable locking and unlocking means 21 positioned on a first side of the securement means 20 for controlling the pivotal orientation of the associated retractor with respect to the mentioned plane.

There is also provided second finger-activatable means 22 for releasably locking and unlocking the associated retractor for controlling the linear position of the retractor along its central elongated axis relative to the securement means 20. The second finger-activatable means 22 is located on a second side of the securement means 20 which is opposite the mentioned first side.

The housing 11 is provided with a rotatable hand knob 23 connected upwardly therefrom. Rotation of the hand knob 23 causes the moveable toothed arm 8 to move along the toothed cross bar 5. An example of a suitable internal mechanism for accomplishing this is shown in U.S. Pat. No. 5,167,223, FIGS. 2–6, which is incorporated herein by reference thereto.

Because a primary object of the present invention is to permit a surgical procedure with a very small incision and a minimum of persons assisting the surgeon, it is necessary to use the specially-designed, shaped, dimensioned and proportioned devices of the invention. In this connection, attention is directed to the self-retaining surgical retractors 13–17 shown in FIG. 5.

Each retractor 13–17 has a blade portion 24–28 and a positioning portion 29–33, respectively. The blade portion 24, 25, 26, 27 or 28 has its major central longitudinal axis forming an obtuse angle relative to the major central longitudinal axis of its associated positioning portion 29, 30, 31, 32 or 33, respectively. Preferably, but not necessarily, the obtuse angle is between 95° and 110°.

The positioning portion 29–33 is preferably, but not necessarily, provided with a series of serrated or sawtoothed teeth 34 to facilitate selective positioning of the retractor.

Figure 5:
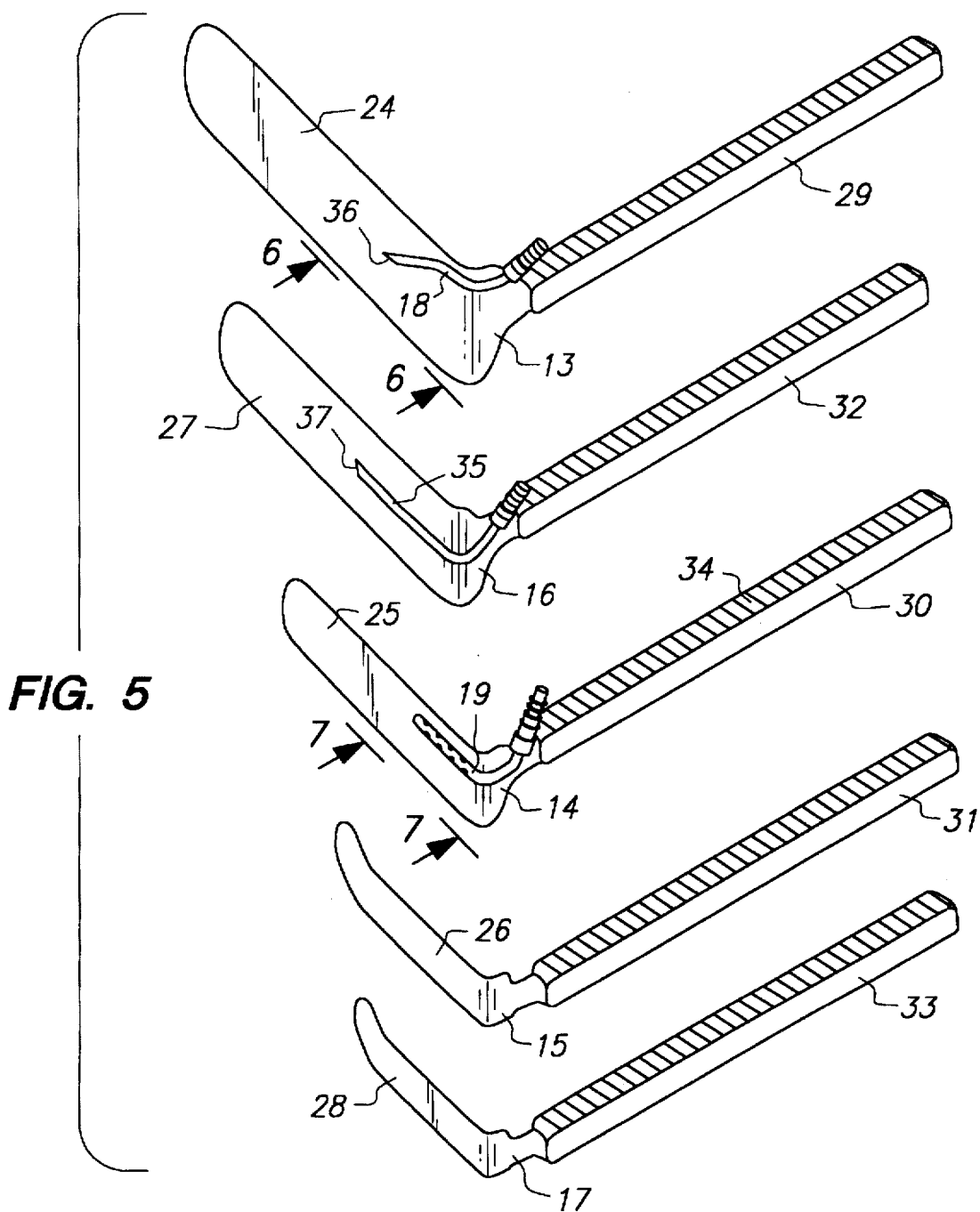
FIG. 5 shows the various types and sizes of self-retaining retractors according to the invention.

It should be noted that FIG. 5 shows a series of different sized retractors which are necessary for use in performing different types of surgeries and/or for use on patients of various size. Smaller sized retractors may be used for smaller sized persons, and larger size retractors for larger sized persons.

FIG. 5 shows two retractors 13 or 16 having fiber optic lighting devices 18 or 35, respectively, unitary therewith. The lighting device 18 or 35 includes a light-radiating portion 36 or 37 which is oriented preferably, but not necessarily, oblique relative to the major edges of its associated retractor.

Figure 6:
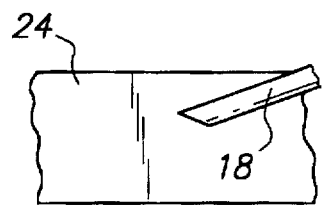
FIG. 6 is a partial fragmentary view taken along the line 6—6 in FIG. 5 to show the arrangement of the lighting device relative to the retractor blade.

On the retractor 13 shown in FIGS. 5 and 6, the lighting device 18 angles in from one edge of the blade 24 towards the center. On another retractor 16 the lighting device 35 may preferably, not not necessarily, be disposed closer to the centerline of the blade 27 but still has an oblique light-radiating portion 37.

Figure 7:
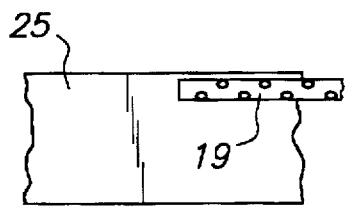
FIG. 7 is a partial fragmentary view taken along the line 7—7 of FIG. 5 to show the arrangement of the suction device relative to the retractor blade.

FIG. 7 shows the suction means 19 unitarily fixed to the blade 25 of a retractor 14.

FIGS. 2, 3 and 4 show securement means apparatus 20 for selectively securing an associated retractor 13, 14, 15, 16 or 17 to stationary arm 2, cross bar 5, or moveable arm 8 (FIG. 1). There is provided a first housing 38 having a first channel 39 therein for securement to, for example, stationary arm 2 having teeth 40 disposed along at least one side or edge thereof. A second housing 42 is pivotally secured to the first housing 38.

Second housing 42 has a toothed sector 43 depending therefrom and being provided with a channel 44 through which retractor 13 having sawtooth teeth 34 disposed along one side thereof may be disposed. The second housing 42 is provided with the first finger-activatable control mechanism 21 which permits releasably locking and unlocking of retractor 13 in a desired position relative to the second housing 42. The first finger-activatable control mechanism 21 is disposed on a first side of the second housing 42.

The second finger-activatable control mechanism 22 is disposed on a second side of the second housing 42 which is opposite to the first side thereof. The first housing 38 has a second channel 45 therein for accommodating the toothed sector 43 and being dimensioned so that no portion of the toothed sector 43 will protrude through the smooth surface 46 of the first housing 38 which is remote from the second housing 42. This prevents the toothed sector 43 from interfering with, damaging or cutting the skin or flesh of the patient.

The first housing 38 is also provided with a spring-biased latching member 47 which is adapted to releasably latch with the teeth 48 of the toothed sector 43. The second finger-activatable control mechanism 22 is operable to control and move the spring-biased latching member 47. A leaf spring 52 is affixed to one end of member 47, is disposed between member 47 and housing 38, and bears against housing 38.

The securement means 20 may preferably, but not necessarily, be provided with a screw clamp or thumbscrew 49 (FIGS. 1 and 4) for selectively, releasably affixing the securement means 20 to member 2, 5 or 8.

FIG. 3 is a partial fragmentary view showing the integral pin 50 which mates the concavities between the teeth of members 2, 5 or 8.

With respect to FIG. 5, it should be noted that the ends of the retractor blades 24-28 are slightly curved inwardly.

As an alternative to the hand knob 23 arrangement shown in FIG. 1, there may be provided a device or knob which the surgeon merely presses to permit the moveable bar to be moved along the cross bar 5, and then releases to lock bars 5 and 8 in the desired position.

With reference to FIG. 5, for sake of clarity various sets of retractors have not been shown. However, it should be appreciated that a set of retractors of a certain size may be provided depending upon the surgical procedure to be performed and/or the size of the patient. For example, there may be one set of sized retractors for performing gall bladder operations or operations in the stomach area, and a second set of larger retractors used for other surgeries, as for example in the pelvic area.

In performing the operation, after the incision has been made, a first retractor 13 is inserted at a desired reference point on the stationary bar 2. Then, a second retractor 14 may be inserted and positioned on the moveable bar 8 in a position substantially opposite of the first retractor 13. The retractors herein have been referred to as self-retaining because it is the body of the patient or his internal organs or tissue which have been pushed out of the normal positions and thus provide a traction force to hold the retractors and the entire apparatus 1 in place.

For most operations two retractors will be sufficient. However, a third retractor such as, spreader 15, may be used if desired. Where necessary, more than one retractor may be secured to the same arm or bar.

It is significant to note that by pivoting or tilting the retractors, the internal organs are pushed back to give a relatively large and variable operating field or volume through a very small incision. Also, the operating field can be varied by translating and/or pivoting the retractors and/or by moving the moveable bar 8 with its associated retractor. Thus, more or less space for the surgeon to work in may easily be provided. The main object of the invention is to provide better access for an operating procedure through a very small opening or incision.

The invention provides variable and expanded internal operating field and light directly into the operating field, as opposed to relying on external sources, e.g., overhead surgical room lights or lights affixed to various portions of the surgeon. Furthermore, the apparatus requires only one surgeon, and does not require assisting personnel to move external lights, to provide suction, to move retractors, etc. The suction means 19 fixed to the retractor blade 25 adequately removes smoke and/or fumes from cautery and laser surgical procedures.

The apparatus 1 rests on the patient without clamps to the patient. The pressure of internal organs and tissue on the retractor blades hold the apparatus 1 in place.

The securement means 20 is dimensioned large enough to be easily grasped by the hand of the surgeon to move and/or activate the devices thereon. The large dimensions of the securement means 20 also permit easier cleaning thereof. The securement means 20 is also provided with a smooth bottom surface 46 to avoid skin damage or abrasion.

The fiberoptic lighting devices 18 or 35 may preferably, but not necessarily, be provided with a single source light powered tube which branches into two separate fiberoptic tubes for providing light to lighting devices 18 or 35. One of such fiberoptic lighting tubes 51 is shown in FIG. 1. The lighting device 18 or 35 may preferably, but not necessarily, be angled towards the center of the blade, and preferably, but not necessarily, may extend down the blade approximately 2-3 centimeters.

With reference to FIGS. 2 and 4, it should be noted that the first housing 38 is provided with a large opening 53 for easier and smoother sliding connection of the securement means 20 to its associated member 2, 5 or 8. The opening 53 is provided by first chamfered surface 54, a second chamfered surface 55, and a lower jaw member 56 which protrudes beyond an upper jaw member 57.

With reference to the sets of retractors, the length and width of the blade in each set is the same, but different between different sets.

While this invention has been described fully and completely, it should be understood that, within the scope of the appended claims, the invention may be practiced otherwise than as specifically described or illustrated.

I claim:

1. A combination self-retaining surgical retractor, lighting device, and suction means apparatus, comprising:

a substantially stationary toothed arm having a first end and a second end;

a toothed cross bar also having a first end and a second end;

said toothed cross bar first end being secured to said first end of said substantially stationary toothed arm in a generally perpendicular relation and forming a generally L-shaped section;

a moveable toothed arm having a first end and a second end;

said first end of said moveable toothed arm having a housing with a slotted opening which is attachable to said toothed cross bar and is laterally moveable along the length of said cross bar;

a plurality of self-retaining surgical retractors;

a lighting device which is unitary with at least one of said self-retaining surgical retractors;

suction means which is unitary with at least one of said self-retaining surgical retractors; and each of said self-retaining surgical retractors being releasably securable to said substantially stationary toothed arm, said toothed cross bar, or said moveable toothed arm.

2. Apparatus according to claim 1, including:

securement means for releasably and moveably securing an associated self-retaining surgical retractor to said substantially stationary toothed arm, said toothed cross bar, or said moveable toothed arm; and said securement means permits moveable positioning of said associated self-retaining retractor including pivotal motion of said associated retractor with respect to a plane containing said substantially stationary toothed arm, said toothed cross bar, and said moveable toothed arm.

3. Apparatus according to claim 2, including:

first finger-actuatable locking and unlocking means positioned on a first side of said securement means for controlling the pivotal orientation of said associated retractor with respect to said plane;

second finger-actuatable means for releasably locking and unlocking said associated retractor for controlling the position of said retractor along its central elongated axis relative to said securement means;

said second finger-actuatable means being located on a second side of said securement means which is opposite said first side; and said lighting device includes a fiberoptic carrier.

4. Apparatus according to claim 2, wherein:

said lighting device includes a fiberoptic light carrier.

5. Apparatus according to claim 2, wherein:

said lighting device includes a light radiating portion which is oriented obliquely to major edges of its associated retractor.

6. Apparatus according to claim 5, wherein:

said lighting device includes a fiberoptic light carrier.

7. Apparatus according to claim 2, including:

a rotatable hand knob upwardly connected with said housing; and whereby rotation of said hand knob causes said moveable toothed arm to move along said toothed cross bar.

8. Apparatus according to claim 1, including:

securement means for releasably and moveably securing an associated self-retaining surgical retractor to said substantially stationary toothed arm, said toothed cross bar, or said moveable toothed arm;

said securement means permits moveable positioning of said associated self-retaining retractor including pivotal motion of said associated retractor with respect to a plane containing said substantially stationary toothed arm, said toothed cross bar, and said moveable toothed arm; and first finger-actuatable locking and unlocking means positioned on a first side of said securement means for controlling the pivotal orientation of said associated retractor with respect to said plane.

9. Apparatus according to claim 8, including:

second finger-actuatable means for releasably locking and unlocking said associated retractor for controlling the position of said retractor along its central elongated axis relative to said securement means;

said second finger-actuatable means being located on a second side of said securement means which is opposite said first side; and said lighting device includes a light-radiating portion which is oriented obliquely relative to major edges of its associated self-retaining retractor.

10. Apparatus according to claim 9, wherein:

said lighting device includes a fiberoptic light carrier.

11. Apparatus according to claim 8, wherein:

said lighting device includes a fiberoptic light carrier.

12. Apparatus according to claim 1, wherein:

said substantially stationary toothed arm, said toothed cross bar, and said moveable toothed arm each comprise a toothed external member having teeth disposed along at least one edge thereof;

each of said self-retaining surgical retractors has sawtooth teeth disposed along a portion thereof;

said apparatus further includes securement means for releasably and moveably securing an associated one of said surgical retractors to a desired one of said toothed external members, said securement means comprising:

a first housing having a first channel therein for securement to said desired one of said toothed external members;

a second housing pivotally secured to said first housing;

said second housing having a toothed sector depending therefrom and being provided with a channel through which said sawtooth teeth portion of said associated surgical retractor may be disposed;

said second housing being provided with a first finger-activatable control mechanism which permits releasably locking and unlocking of said associated surgical retractor in a desired position relative to said second housing;

said first finger-activatable control mechanism being disposed on a first side of said second housing;

a second finger-activatable control mechanism being disposed on a second side of said second housing which is opposite to said first side thereof;

said first housing having a second channel therein for accommodating said toothed sector and being dimensioned such that no portion of said toothed sector will protrude through a surface of said first housing which is remote from said second housing;

said first housing being provided with a spring-biased latching member which is adapted to releasably latch with the teeth of said toothed sector; and said second finger-activatable control mechanism being operable to move said spring-biased latching member.

13. Apparatus according to claim 1, including:

securement means for releasably and moveably securing an associated self-retaining surgical retractor to said substantially stationary toothed arm, said toothed cross bar, or said moveable toothed arm;

said securement means permits moveable positioning of said associated self-retaining retractor including pivotal motion of said associated retractor with respect to a plane containing said substantially stationary toothed arm, said toothed cross bar, and said moveable toothed arm;

first finger-actuatable locking and unlocking means positioned on a first side of said securement means for controlling the pivotal orientation of said associated retractor with respect to said plane;

second finger-actuatable means for releasably locking and unlocking said associated retractor for controlling the position of said retractor along its central elongated axis relative to said securement means; and said second finger-actuatable means being located on a second side of said securement means which is opposite said first side.

14. Apparatus according to claim 1, wherein:

said lighting device includes a fiberoptic light carrier.

15. Apparatus according to claim 1, wherein:

said lighting device includes a light-radiating portion which is oriented obliquely relative to major edges of its associated retractor.

16. Apparatus according to claim 15, wherein:

said lighting device includes a fiberoptic light carrier.

17. Apparatus according to claim 1, wherein:

each of said self-retaining surgical retractors has a blade portion and a positioning portion; and said blade portion has its major central elongated axis forming an obtuse angle relative to the major central elongated axis of said positioning portion.

18. Apparatus according to claim 1, including:

a rotatable hand knob upwardly connected with said housing; and whereby rotation of said hand knob causes said moveable toothed arm to move along said toothed cross bar.

* * * * *